(12) United States Patent
Kutsovsky

(10) Patent No.: US 7,892,643 B2
(45) Date of Patent: Feb. 22, 2011

(54) METAL AND OXIDES THEREOF AND METHODS TO MAKE SAME

(75) Inventor: Yakov E. Kutsovsky, Arlington, MA (US)

(73) Assignee: Cabot Corporation, Boston, MA (US)

( * ) Notice: Subject to any disclaimer, the term of this patent is extended or adjusted under 35 U.S.C. 154(b) by 912 days.

(21) Appl. No.: 11/240,083

(22) Filed: Sep. 30, 2005

(65) Prior Publication Data

US 2006/0067868 A1 Mar. 30, 2006

Related U.S. Application Data

(60) Provisional application No. 60/614,501, filed on Sep. 30, 2004.

(51) Int. Cl.
| | |
|---|---|
| B32B 5/16 | (2006.01) |
| B32B 9/00 | (2006.01) |
| B32B 15/02 | (2006.01) |
| B32B 17/02 | (2006.01) |
| B32B 19/00 | (2006.01) |
| B32B 21/02 | (2006.01) |
| B32B 23/02 | (2006.01) |
| B32B 27/02 | (2006.01) |
| C01B 33/12 | (2006.01) |
| C01B 13/14 | (2006.01) |
| A61K 8/02 | (2006.01) |
| B60C 1/00 | (2006.01) |
| C08K 3/34 | (2006.01) |
| C08K 3/18 | (2006.01) |
| C08K 3/22 | (2006.01) |
| C09D 11/00 | (2006.01) |

(52) U.S. Cl. ............. 428/402; 423/337; 423/592.1; 424/401; 524/492; 524/430; 106/31.27; 106/31.6; 106/31.9

(58) Field of Classification Search .......... 423/335, 423/337, 592.1–594.6, 595–603, 594.7–594.16, 423/604–643; 502/300–355; 524/492, 430, 524/439; 361/580, 528; 106/31.27, 31.6, 106/31.9; 428/402; 424/401; 420/402–427, 420/435–440, 513–524, 528–554, 557–562, 420/578

See application file for complete search history.

(56) References Cited

U.S. PATENT DOCUMENTS

| | | |
|---|---|---|
| 3,273,962 A | 9/1966 | Walsh |
| 3,649,588 A | 3/1972 | Kennedy-Skipton |
| 3,681,017 A * | 8/1972 | Butcher et al. ........... 423/338 |

(Continued)

FOREIGN PATENT DOCUMENTS

DE 199 49 776 A1 4/2001

(Continued)

OTHER PUBLICATIONS

Fowler et al. "Facile synthesis of hollow silica microspheres", J. Mater. Chem., 2001, 11, 1968-1971.*

(Continued)

*Primary Examiner*—Stanley Silverman
*Assistant Examiner*—Anthony J Zimmer

(57) ABSTRACT

Metal oxides and metals are described. The metal oxides and metals, such as silica, are preferably obtained by removing a removable template to obtain a metal oxide or metal material. Applications and uses of the material are further described.

19 Claims, 1 Drawing Sheet

U.S. PATENT DOCUMENTS

| | | | |
|---|---|---|---|
| 3,765,866 A | 10/1973 | Nayar | |
| 4,123,389 A | 10/1978 | Pieters et al. | |
| 4,162,238 A | 7/1979 | Bergna | |
| 4,251,276 A * | 2/1981 | Ferree et al. | 523/161 |
| 4,503,169 A | 3/1985 | Randklev | |
| 4,588,770 A * | 5/1986 | Wurminghausen et al. | 524/731 |
| 4,708,863 A * | 11/1987 | Bews et al. | 424/47 |
| 4,777,035 A | 10/1988 | Shin | |
| 5,024,826 A * | 6/1991 | Linton | 423/335 |
| 5,114,764 A | 5/1992 | Perrin | |
| 5,356,471 A * | 10/1994 | Reynders | 106/489 |
| 5,360,851 A | 11/1994 | Feder et al. | |
| 5,372,795 A | 12/1994 | Mühlhofer et al. | |
| 5,474,806 A * | 12/1995 | Morgan et al. | 427/223 |
| 5,480,626 A | 1/1996 | Klasen et al. | |
| 5,500,216 A | 3/1996 | Julian et al. | |
| 5,573,584 A * | 11/1996 | Ostertag et al. | 106/417 |
| 5,747,562 A | 5/1998 | Mahmud et al. | |
| 5,749,950 A | 5/1998 | Mahmud et al. | |
| 5,776,240 A | 7/1998 | Deller et al. | |
| 5,830,930 A | 11/1998 | Mahmud et al. | |
| 5,863,323 A | 1/1999 | Mahmud et al. | |
| 5,869,550 A | 2/1999 | Mahmud et al. | |
| 5,877,238 A | 3/1999 | Mahmud et al. | |
| 5,904,762 A | 5/1999 | Mahmud et al. | |
| 5,916,934 A | 6/1999 | Mahmud et al. | |
| 5,919,841 A | 7/1999 | Mahmud et al. | |
| 5,948,475 A | 9/1999 | Hung | |
| 5,948,835 A | 9/1999 | Mahmud et al. | |
| 5,977,213 A | 11/1999 | Mahmud et al. | |
| 5,985,424 A * | 11/1999 | DeMatte et al. | 428/212 |
| 5,998,548 A | 12/1999 | Brennenstuhl et al. | |
| 6,004,525 A | 12/1999 | Tani et al. | |
| 6,017,980 A | 1/2000 | Wang et al. | |
| 6,028,137 A | 2/2000 | Mahmud et al. | |
| 6,057,387 A | 5/2000 | Mahmud et al. | |
| 6,106,926 A * | 8/2000 | Kurz et al. | 428/141 |
| 6,156,468 A | 12/2000 | Wehelie et al. | |
| 6,194,508 B1 | 2/2001 | Achenbach et al. | |
| 6,197,274 B1 | 3/2001 | Mahmud et al. | |
| 6,207,610 B1 * | 3/2001 | Krause et al. | 502/232 |
| 6,211,279 B1 | 4/2001 | Mahmud et al. | |
| 6,235,258 B1 | 5/2001 | Müller et al. | |
| 6,323,273 B1 | 11/2001 | Mahmud et al. | |
| 6,364,944 B1 | 4/2002 | Mahmud et al. | |
| 6,448,309 B2 | 9/2002 | Mahmud et al. | |
| 6,686,409 B2 | 2/2004 | Mahmud et al. | |
| 6,709,506 B2 | 3/2004 | Mahmud et al. | |
| 6,762,147 B2 | 7/2004 | Morikawa et al. | |
| 6,773,814 B2 * | 8/2004 | Hasenzahl et al. | 428/404 |
| 7,008,695 B1 * | 3/2006 | Clough | 428/367 |
| 7,169,261 B2 * | 1/2007 | Persson et al. | 162/181.6 |
| 7,291,216 B2 * | 11/2007 | Bujard | 106/415 |
| RE40,299 E * | 5/2008 | Bruinsma et al. | 423/335 |
| 7,563,317 B2 * | 7/2009 | Meyer et al. | 106/481 |
| 2001/0033818 A1 | 10/2001 | Nozawa et al. | |
| 2001/0036437 A1 | 11/2001 | Gutsch et al. | |
| 2002/0025288 A1 | 2/2002 | Nozawa et al. | |
| 2002/0044903 A1 | 4/2002 | Oswald et al. | |
| 2002/0160912 A1 | 10/2002 | Morikawa et al. | |
| 2003/0031615 A1 * | 2/2003 | Satou et al. | 423/335 |
| 2003/0040553 A1 | 2/2003 | Mahmud et al. | |
| 2003/0124321 A1 | 7/2003 | Schneider et al. | |
| 2003/0125418 A1 * | 7/2003 | Shibusawa et al. | 523/212 |
| 2003/0165728 A1 * | 9/2003 | Meguriya et al. | 429/35 |
| 2004/0241056 A1 | 12/2004 | Nozawa et al. | |
| 2004/0265219 A1 * | 12/2004 | Bauer et al. | 423/625 |
| 2005/0013765 A1 * | 1/2005 | Thomas et al. | 423/592.1 |
| 2005/0074473 A1 * | 4/2005 | Kosbach et al. | 424/401 |
| 2005/0244642 A1 | 11/2005 | Meyer et al. | |

FOREIGN PATENT DOCUMENTS

| | | |
|---|---|---|
| EP | 166009 A1 * | 1/1986 |
| JP | 10-030067 | 3/1998 |
| WO | WO 02/074431 A1 | 9/2002 |
| WO | WO 03068868 A2 * | 8/2003 |

OTHER PUBLICATIONS

Iarlori et al. "Dehyroxylation and Silanization of the Surfaces of beta-cristobalite silica: An ab Initio Simulation", J. Phys. Chem. B 2001, 105, 8007-8013.*

European Search Report from European Patent Application No. 05 816 307.2-2111, dated Feb. 29, 2008, nine pages.

International Preliminary Report on Patentability and Written Opinion of the International Searching Authority for PCT/US2005/035387 dated Apr. 12, 2007.

International Search Report for PCT/US2005/035387 dated Oct. 20, 2006.

Jacobsen et al., "Mesoporous Zeolite Single Crystals," Journal of the American Chemical Society, vol. 122, No. 29, Jul. 26, 2000, pp. 7116-7117.

Ajayan et al., "Carbon Nanotubes as Removable Templates for Metal Oxide Nanocomposites and Nanostructures," Nature, vol. 375, Jun. 15, 1995, pp. 564-567

Wang, et al., "New Generation Carbon-Silica Dual Phase Filler Part I. Characterization and Application to Passenger Tire," Rubber Chemistry and Technology, May-Jun. 2002, pp. 247-263, vol. 75, No. 2.

Office Action from the U.S. Patent and Trademark Office dated Feb. 10, 2009 received in corresponding U.S. Appl. No. 11/825,110 (20 pages).

Final Office Action issued by the U.S. Patent and Trademark Office for U.S. Appl. No. 11/825,110 dated Feb. 5, 2010 (14 pages).

* cited by examiner

METAL AND OXIDES THEREOF AND METHODS TO MAKE SAME

This application claims the benefit under 35 U.S.C. §119(e) of prior U.S. Provisional Patent Application No. 60/614,501 filed Sep. 30, 2004, which is incorporated in its entirety by reference herein.

FIELD OF THE INVENTION

The present invention relates to silica, other metal oxides, and metals and methods to make various forms of silica, other metal oxides, and metals. The present invention further relates to the use of the silica, other metal oxides, and metals in compositions, such as elastomeric compositions and other compositions that contain conventional metal oxides or metals.

Silica has been used for a number of years in a variety of compositions as a filler or for other reasons such as to improve certain properties such as a reinforcing agent and the like. Generally, most silica has a spherical shape or aggregated spherical shape and is generally limited to this shape due to the manner in which the silica is obtained.

Accordingly, there is always a desire in the industry to improve upon the properties of the silica so that the silica may better enhance the composition that it is used in. The same is also true for metal oxides and metals in general.

SUMMARY OF THE INVENTION

An object of the present invention is to provide a new form of silica which generally is not spherical.

Another feature of the present invention is to provide a method of making silica which permits the formation of unique shapes of silica.

A further feature of the present invention is to provide metals and oxides thereof having unique morphology and/or shape.

A further feature of the present invention is to provide a method to make metal and/or oxides thereof having unique morphologies and/or shapes.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method of making silica, other metal oxides, or a metal by taking an aggregate comprising at least a carbon phase and a silicon-containing species phase or a metal-containing species phase or a metal or metal oxide-coated carbonaceous material and removing the carbon phase to form essentially an aggregate or material that is solely the silicon-containing species phase or metal-containing species phase. In the preferred embodiment, the remaining silicon-containing species phase is silica. Preferably, the method of forming the silica, other metal oxides, or metal is with the use of a multi-stage feedstock injection system as described below.

In one or more embodiments, the present invention further relates to a pyrogenic metal or oxide thereof, such as pyrogenic silica, and/or can have a BET surface area of at least 1,050 $m^2/g$, and/or can have a shape of a curved platelet.

The present invention further relates to a method of making silica, other metal oxides, or a metal by using a removable template on which the silica, other metal oxide, or metal is formed or placed, and then removing the removable template to obtain the silica, other metal oxides, or metal. The removable template can have any desirable shape.

In addition, the present invention relates to a variety of uses for the metal or oxide thereof of the present invention, including cosmetic uses, household uses, pharmaceutical uses, and the like. The material of the present invention can act as a liquid carrier or provide release characteristics desirable to a variety of products.

It is to be understood that both the foregoing general description and the following detailed description are exemplary and explanatory only and are intended to provide a further explanation of the present invention, as claimed.

BRIEF DESCRIPTION OF THE DRAWING

The FIGURE is a schematic view of a portion of one type of a multistage reactor which may be used to produce the aggregates of the present invention.

DETAILED DESCRIPTION OF THE INVENTION

Figure 1:
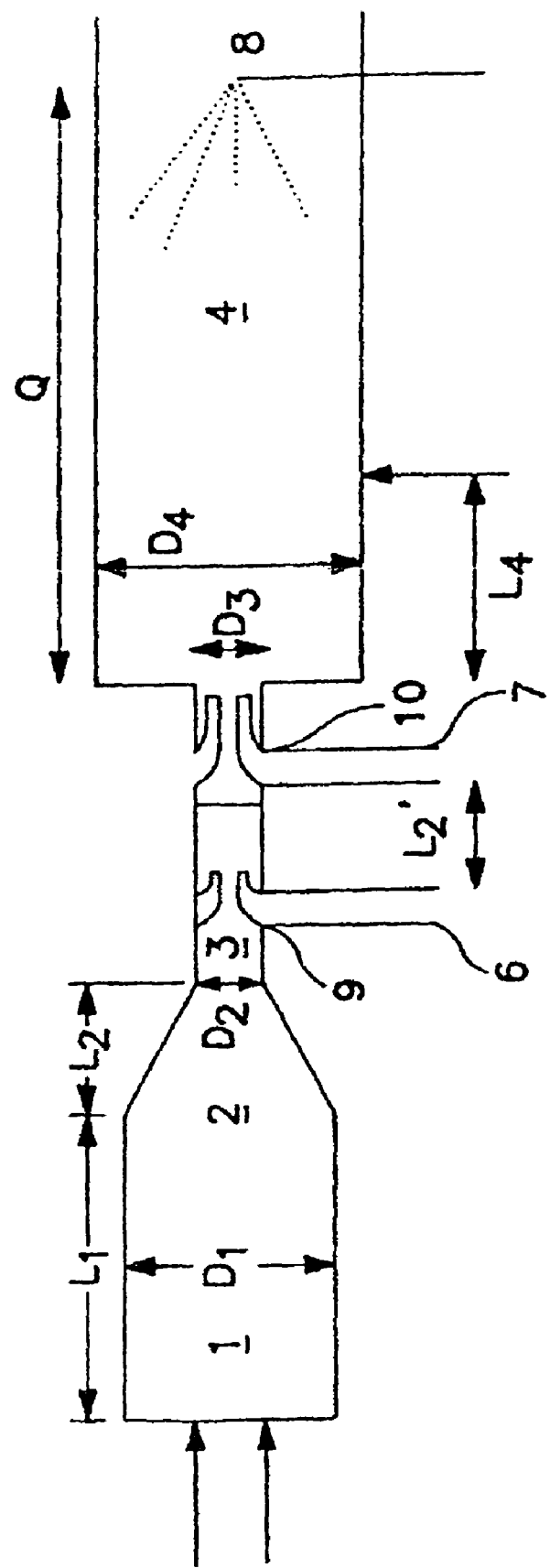

The present invention relates to silica, other metal oxides, and metals and to a method of making these products.

With respect to the shape, the metal oxide or metal, such as silica, preferably has a shell-like shape or structure. The metal or oxide thereof is preferably not spherical in shape. For instance, the metal or oxide thereof can have a molded shell type appearance which may be also in the form of broken or irregular or partial shells. Another way to describe the various types of metal or oxide thereof of the present invention is that it is typically a platelet shape which generally is non-linear but is curved. In other words, one preferred shape of the metal or oxide thereof is a curved platelet. For purposes of the present invention, the preferred embodiment, namely silica, is discussed in detail. However, it is to be realized that silica is a metal oxide and that the present invention also relates to metals and metal oxides other than silica. Accordingly, the characteristics with regard to shape and other parameters and uses equally applies in general to metals and oxides thereof.

The metal or oxides thereof (e.g., silica) of the present invention, in one embodiment, can have an aspect ratio of from 2 to 150 and more preferably from 5 to 100. The aspect ratio is defined as the ratio of a length and width of platelet or a shell to its thickness t. The thickness t is defined on the basis of BET of the shell material and the true density of the shell or platelet rho as t $[nm]=6000/(BET[m^2/g]*rho[g/m^3])$.

In one or more embodiments of the present invention, the material of the present invention, e.g., silica, metal oxides other than silica, or metals can be considered pyrogenic. In other words, in the preferred embodiment, the silica is pyrogenic silica. Thus, the silica is not precipitated silica. Further, the material of the present invention can be considered a fumed product, such as fumed silica ash.

The material of the present invention can have any one or more of the characteristics discussed herein. For instance, the material of the present invention, such as silica, can be a pyrogenic silica, which can have a surface area in the ranges described herein and/or can be in the shape of a curved platelet. The material of the present invention, such as silica, can have a shape that is greater than a half sphere.

Also or alternatively, the material of the present invention, and preferably silica, can have a DBP absorption in any suitable range. For instance, the DBP absorption can be from about 400 to about 1000 ml/100 g and, more preferably, from about 550 to about 850 ml/100 g.

Further, the metal or oxides thereof (e.g., silica) of the present invention can have a BET surface area of from about 100 to about 1,000 m$^2$/g or more, and more preferably from about 300 to about 700 m$^2$/g. The BET surface area can be from 1,050 m$^2$/g to 1,500 m$^2$/g or higher. The material of the present invention can have any surface area.

In one or more embodiments of the present invention, the metal oxide(s) of the present invention can have a S-factor of from about 0.05 to about 0.98 (e.g., from 0.1 to 0.9, from 0.25 to 0.9, from 0.35 to 0.85, from 0.5 to 0.9 or from 0.6 to 0.8 and so on). The S-factor is defined as one minus the ratio of the Iodine adsorption number (mg/g) and BET surface area (m$^2$/g) of the starting material as:

$$S=1-(I_2\text{No}/\text{BET})$$

The iodine in the Iodine adsorption number test does not adsorb on the silica surface. A comparative example is that I$_2$No on fumed silica HS-5 that has BET surface area of 340 m$^2$/g has negligible I$_2$No of 0.5. The S-factor can be used as one way in this invention to define the completeness of the shell that results after the carbon phase or other removable template is removed. When the S factor is small, the silica (or metal oxide or metal) containing phase would track the portions of the shape of the template and produce incomplete shells (e.g., forming curved platelets), and when the S factor is high and close to 1 the silica (or metal oxide or metal) containing phase will track substantially the shape of the template and produce a more complete shell. Compressed DBP oil adsorption measurements (CDBP) of the starting material can be used to estimate the structure of the template.

In general, the metal oxides and metals can have one or more of the above characteristics. In addition, or as an option, the metal or oxides thereof of the present invention can have other characteristics.

The present invention, in one or more embodiments, relates to a method of making metal or oxides thereof (e.g., silica), which involves providing a metal or oxides thereof (e.g., silica) on a removable template and then removing the removable template to obtain the metal or oxides thereof (e.g., silica).

Essentially, for purposes of the present invention, any starting material that has a removable template, such that when the template is removed, metal or oxides thereof (e.g., silica), is recovered, can be used. For instance, a carbon product, such as carbon black, having a silica coating on the carbon product can be used, wherein the carbon product is removed to obtain the silica. The recovered metal or oxide thereof will generally have the shape of the external surface of the template if the metal or oxide thereof is located on the surface of the template. The template can have any shape, such as particle or agglomerate shapes, like spherical or clustered particle shapes. The template can have particle sizes of from about 10 nm to about 500 nm or more, and preferably from about 50 nm to about 200 nm.

In addition, the present invention relates to a method of making the metal or oxides thereof (e.g., silica). One method to make the products of the present invention involves taking an aggregate comprising a carbon phase and a silicon-containing species phase or metal-containing species phase or both and removing the carbon phase to obtain metal or oxides thereof (e.g., silica).

With respect to the removable template, the template can be essentially any carbon-based material, including inorganic or organic materials, such as polymers, minerals, carbon products such as carbon black, activated carbon, nanotubes, carbon fibers, and the like. Any template can be used wherein the template is removable, such as by heat, without damage to the material recovered. In other words, any template material can be used as long as the template can be removed without damaging or removing the metal or oxides thereof (e.g., silica). The amount of template can be any amount depending upon the desired shape and morphology of the remaining product, namely the metal or oxides thereof (e.g., silica). Also, the amount of metal or oxides thereof (e.g., silica) present with the removable template can be any suitable amount, such as from 0.1 wt % to 95 wt % or more, based on the weight of the starting material. With the present invention, the amounts of metal or oxides thereof (e.g., silica) can be altered along with the amount of template material to achieve the various morphology and shapes desired for particular applications. In at least one embodiment, the removable template used in the present invention can have a t-area of 120 m$^2$/g or less or a t-area of from 155 m$^2$/g or more, such as from 160 m$^2$/g to 500 m$^2$/g or more. In one or more embodiments, the starting material (e.g., the multi-phase aggregate) can have a CDBP of 99 ml/100 g or less or a CDBP of from 105 ml/100 g or more, such as 30 ml/100 g to 90 ml/100 g or 110 ml/100 g to 300 ml/100 g. Preferably, the removable template is a carbon product, such as carbon black (or carbon phase) and the carbon black can have these t-areas for purposes of the template.

In the embodiment that uses the multi-phase aggregate as the starting material, the aggregate comprising a carbon phase and a silicon-containing species phase can also be identified as a silicon-treated carbon black. In the aggregate comprising a carbon phase and a silicon-containing species phase, a silicon-containing species, including but not limited to, oxides and carbides of silicon, may be distributed through at least a portion of the aggregate and is an intrinsic part of the aggregate which also contains the carbon phase. In other words, the silicon-treated carbon black or the aggregate does not represent a mixture of discrete carbon black aggregates and discrete silica aggregates. Rather, the silicon-treated carbon black of the present invention includes at least one silicon-containing region as part of the silicon-treated carbon black wherein the silicon-containing region is located at the surface of and/or within the silicon-treated carbon black. The silicon-containing species that is part of the aggregate of the present invention is not attached to a carbon black aggregate like a silane coupling agent, but actually is part, of the same aggregate as the carbon phase. The disclosures of U.S. Pat. Nos. 6,008,272; 5,916,934; 5,904,762; 6,057,387; 6,191,194; 5,830,930; 5,877,238; 5,948,835; 6,028,137; 6,017,980; 6,323,273; 6,709,506; 6,686,409; 6,469,089; 6,364,944; and 6,211,279 are incorporated in their entirety herein by reference.

When the silicon-treated carbon black is examined under scanning transmission electron microscope-energy dispersive x-ray (STEM-EDX), the silicon signal corresponding to the silicon-containing species is found to be present in individual carbon black aggregates. By comparison, for example, in a physical mixture of silica and carbon black, STEM-EDX examination reveals distinctly separate silica and carbon black aggregates.

With regard to a process of the present invention, the aggregates or the silicon-treated carbon blacks of the present invention may be obtained by manufacturing or forming the carbon black (i.e., the carbon phase) in the presence of one or more volatilizable and/or decomposable silicon-containing compounds. A modular or "staged," furnace carbon black reactor as depicted in the FIGURE is preferably used. The furnace or reactor preferably has more than one stage or entry point for feedstocks. As depicted in the FIGURE, the reactor preferably has a combustion zone 1, with a zone of converging diameter 2; a feedstock injection zone with restricted diameter 3; and a reaction zone 4.

To produce the aggregates or the silicon-treated carbon blacks of the present invention with the reactor described above, hot combustion gases are generated in combustion zone 1 by contacting a liquid or gaseous fuel with a suitable oxidant stream such as air, oxygen, or mixtures of air and oxygen. Among the fuels suitable for use in contacting the oxidant stream in combustion zone 1, to generate the hot combustion gases, are included any readily combustible gas, vapor, or liquid streams such as natural gas, hydrogen, methane, acetylene, alcohols, or kerosene. It is generally preferred, however, to use fuels having a high content of carbon-containing components and in particular, hydrocarbons. The ratio of air-to-fuel varies with the type of fuel utilized. When natural gas is used to produce the carbon phase of the present invention, the ratio of air-to-fuel may be from about 10:1 to about 1000:1. To facilitate the generation of hot combustion gases; the oxidant stream may be pre-heated. U.S. Pat. Nos. 3,952,087 and 3,725,103 are incorporated in their entirety by reference and describe carbon black-yielding feedstocks, reactor set-up, and conditions.

The hot combustion gas stream flows downstream from zones 1 and 2 into zones 3 and 4. The direction of the flow of hot combustion gases is shown in the FIGURE by the arrow. A first feedstock is introduced at location 6 and enters the feedstock injection zone 3 at entry point 9. In this embodiment, the feedstocks are introduced or injected into a preformed stream of hot combustion gasses flowing in a downstream direction. While the FIGURE depicts entry points 9 and 10 for introduction of the feedstock, the feedstocks can be introduced at any point in the reactor as long as there is a sufficient temperature and residence time for the silicon-treated carbon black to form before the quench location. The feedstock is injected into the gas stream preferably through nozzles designed for optimal distribution of the oil in the gas stream. Such nozzles may be either single or bi-fluid. Bi-fluid nozzles may use steam or air to atomize the fuel. Single-fluid nozzles may be pressure atomized or the feedstock can be directly injected into the gas stream. In the latter instance, atomization occurs by the force of the gas stream.

In an embodiment of the present invention, the first feedstock comprises a carbon black-yielding feedstock, a silicon-containing compound, or a mixture thereof. Also, the first feedstock, as well as all of the feedstocks described hereinafter, may further comprise additional materials or compositions which are commonly used to make conventional carbon black. One or more feedstocks can also contain a boron-containing compound.

Located downstream of the point where the first feedstock is introduced into the feedstock injection zone 3 of the reactor, a second feedstock is introduced, for example, through location 7 into the feedstock injection zone 3. The second feedstock can enter the feedstock injection zone for instance, at entry point 10. The second and subsequent feedstocks are preferably added at the zone of substantial reaction, which is where the earlier feedstocks will primarily react to form the aggregates. The second feedstock comprises a carbon black-yielding feedstock, a silicon-containing compound, or a mixture thereof. As in the case of the first feedstock, other additional compounds or materials can also be included as part of the feedstock. Furthermore, the first feedstock and the second feedstock can be the same or different with respect to feedstocks.

When a two-stage reactor is used, for purposes of an embodiment of the present invention, if the first feedstock contains a carbon black-yielding feedstock (without a silicon-containing compound), then the second feedstock comprises either a mixture of a carbon black-yielding feedstock and a silicon-containing compound or a silicon-containing compound alone. In other words, one or both feedstocks may contain a carbon black-yielding feedstock, and at least one feedstock will additionally contain a silicon-containing compound.

In addition, additional feedstocks can be introduced into the feedstock injection zone by additional entry points which can be located downstream of the first and/or second entry points for the first and second feedstocks. If necessary, a reactor can be modified to lengthen the feedstock injection zone to accommodate the additional entry points.

For purposes of the present invention where a two-stage reactor is used to make an aggregate comprising a carbon phase and a silicon-containing phase, at least one of the feedstocks must include a carbon black-yielding feedstock and at least one of the feedstocks must contain a silicon-containing feedstock. Thus, and only as an example, the first feedstock can include a mixture of a carbon black-yielding feedstock and a silicon-containing compound while the second feedstock can also include either a mixture of a carbon black-yielding feedstock and a silicon-containing compound or a silicon-containing compound only. The first feedstock and the second feedstock can both include a carbon black-yielding feedstock and the second feedstock can also include a silicon-containing compound. Accordingly, almost any combination of feedstocks is possible in the two-stage process as long as a carbon black-yielding feedstock and a silicon-containing compound are present either in the same or different feedstocks. As stated earlier, in a two-stage process, when the first feedstock comprises a carbon black-yielding feedstock (without a silicon-containing compound), then the second feedstock comprises a mixture of a carbon black-yielding feedstock and a silicon-containing compound or silicon-containing compound alone.

It is preferred that the first feedstock comprises a carbon black-yielding feedstock and that at least about 5% by weight of the total amount of carbon black-yielding feedstock used in the process is present in the first feedstock. More preferably, from about 10% by weight to about 100% by weight, and even more preferably, from about 40% by weight to about 100% by weight of the total amount of carbon black-yielding feedstock used in said method is present in the first feedstock.

In another embodiment of the present invention, the aggregate or silicon-treated carbon black of the present invention can be made using a multi-stage reactor, wherein the reactor has at least three stages for introducing feedstocks into the reactor. The second and third stages, as well as any additional stages, are located downstream of the first stage. As stated earlier, these stages can be located anywhere downstream as long as there is a sufficient temperature and residence time for the silicon-treated carbon black to form before any quenching occurs. Each of the feedstocks introduced into the stages comprises a carbon black-yielding feedstock, a silicon-containing compound, or a mixture thereof. At least one of the stages comprises a carbon black-yielding feedstock and at least one of the stages, which can be the same stage containing the carbon black-yielding feedstock, comprises a silicon-containing compound. The reactor is maintained at a sufficient temperature to decompose the silicon-containing compound and to pyrolize the carbon black-yielding feedstock.

Referring to the FIGURE again, the mixture of feedstocks and hot combustion gases flows downstream through zones 3 and 4. In the reaction zone portion of the reactor, the portion of the feedstock which contains the carbon black-yielding feedstock is pyrolyzed to carbon black to form the carbon phase of the aggregate. The feedstock portion containing the silicon-containing compound undergoes volatilization and decomposes, and preferably reacts with other species in the reaction zone and forms a silicon-containing species phase. The presence of the carbon black-yielding feedstock and the silicon-containing compound in the reactor leads to the aggregate comprising a carbon phase and a silicon-containing species phase. The silicon-containing species are an intrinsic part of the aggregate and are part of the same aggregate as the carbon phase. An example of a silicon-containing species is silica. Besides volatilizable compounds, decomposable compounds which are not necessarily volatilizable can also be used to yield the silicon-containing species phase of the aggregates of the present invention.

The reaction in the reaction zone is then arrested in the quench zone of the reactor. Quench 8 is located downstream of the feedstock entry points and the reaction zone and sprays a quenching fluid, generally water, into the stream of newly formed aggregates or silicon-treated carbon black and any carbon black and/or silica that may also be present. The quench serves to cool the aggregates or particles and to reduce the temperature of the gaseous stream and decrease the reaction rate. Q is the distance from the beginning reaction zone 4 to quench 8 and will vary according to the position of the quench. Optionally, quenching may be staged, or take place at several points in the reactor.

After the aggregates or particles are quenched, the cooled gases and the aggregates pass downstream into any conventional cooling and separating means whereby the aggregates and any co-produced carbon black and/or silica are recovered. The separation of the aggregates from the gas stream is readily accomplished by conventional means such as a precipitator, cyclone separator, bag filter, or other means known to those skilled in the art. After the aggregates have been separated from the gas stream, they are optionally subjected to a pelletization step.

Useful volatilizable silicon-containing compounds include any such compound which is volatilizable at carbon black reactor temperatures. Examples include, but are not limited to, silicates such as tetraethoxyorthosilicate (TEOS) and tetramethoxyorthosilicate, silanes for example alkoxysilanes, alkylalkoxysilanes and aryl-alkylalkoxysilanes, for example, tetramethoxysilane, tetraethoxysilane, methyltrimethoxy-silane, methyltriethoxy silane, dimethyldimethoxysilane, dimethyldiethoxysilane, trimethylmethoxysilane, trimethylethoxysilane, diethylpropylethoxysilane, halogen-organosilanes for examples, tetrachlorosilane, trichloromethylsilane, dimethyl-dichlorosilane, trimethylchlorosilane, methyethyldichlorosilane, dimethylethylchlorosilane, dimethyethylbromosilane, silicone oil, polysiloxanes and cyclic polysiloxanes for example, octamethylcyclotetrasiloxane (OMTS), decamethylcyclopentasiloxane, dodecamethylcyclohexasiloxane, hexamethyl-cyclotrisiloxane, and silazanes for example, hexamethyldisilazane. Besides volatilizable compounds. decomposable silicon-containing compounds which are not necessarily volatilizable can also be used to yield the silicon-treated carbon black. Silicon-containing compounds which may be used are set forth in Encyclopedia of Science and Engineering, Vol. 15, 2nd Ed pp. 204-308, and UK Patent Application 2 296 915, both incorporated herein by reference. The usefulness of these compounds can be readily determined for their volatilizability and/or decomposability. Low molecular weight silicon-containing compounds are preferred. The flow rate of the volatilizable compound will determine the weight percent of silicon in the silicon-treated carbon black.

Generally, if the silicon-containing compound is introduced substantially simultaneously with the carbon black-yielding feedstock, the silicon-containing species phase(s) are distributed throughout the aggregate. If the silicon-containing compound is introduced to the reaction zone at a point after the carbon black formation has commenced (i.e., during the formation of the carbon phase), but before the reaction stream has been subjected to the quench, the silicon-containing species phase is present primarily at or near the surface of the aggregate but is still part of the same aggregate as the carbon phase.

In general, the multi-phase aggregates of the present invention can be used either in nonagglomerated form, i.e., fluffy, or in agglomerated form. The multi-phase aggregate can be agglomerated in wet or dry processes as known in the art. During the wet agglomeration process, different types of pelletizing agents (e.g., binders and the like) can be added to the pelletizing water, see e.g. WO 96/29710, incorporated herein by reference.

The weight percent of silicon in the silicon-treated carbon black preferably ranges from about 0.1% to about 95%, such as from about 0.5% to about 50% by weight of the aggregate.

At least one diluent can be present in any feedstock including the silicon-containing compound. The diluent should be volatilizable and/or decomposable since it will be preferably injected into the reactor along with the silicon-containing compound. The diluent can as well also serve as a carbon black-yielding feedstock. For instance, the diluent can comprise alcohol or mixtures thereof which can serve as the carbon black-yielding feedstock as well as the diluent. The diluent is preferably capable of increasing the mass flow rate of the feedstock in which it is contained and/or is capable of lowering the temperature of the reactor at about the point of introduction of the feedstock which contains the diluent. The lower temperature assists in causing the silica domain aggregate to be finer and more numerous. The diluent can comprise a liquid and/or a gas and is preferably miscible with the silicon-containing compounds though this is not necessary. Further examples of diluents are water and aqueous based solutions. The diluent can be present in any amount and is preferably present in amounts which will increase the mass flow rate of the feedstock and/or lower the temperature of the reactor at about the point of introduction of the feedstock. The diluent can also be included in feedstocks which do not contain any silicon-containing compound, or can be introduced in a separate stage.

In a further embodiment of the present invention, an aggregate comprising a carbon phase and a metal-containing species phase can be made also using a multi-stage reactor, wherein the reactor has at least two stages for introducing the feedstocks into the reactor. The second, as well as any additional stages, are located downstream of the first stage. Each of the feedstocks introduced into the stages comprise a carbon black-yielding feedstock, a metal-containing compound, or a mixture thereof. At least one of the feedstocks comprises a carbon black-yielding feedstock and at least one of the feedstocks, which can be the same stage containing the carbon black-yielding feedstock, comprises a metal-containing compound. In addition, any one of the feedstocks further comprise a silicon-containing compound and/or boron-containing compound. The reactor is maintained at a temperature sufficient to decompose the metal-containing compound and to form a carbon phase (i.e., pyrolize the carbon black-yielding feedstock). If any silicon-containing compound or boron-containing compound is additionally present, the reactor should be also maintained at a temperature sufficient to decompose the silicon-containing compound or boron-containing compound. The aggregate formed by this process can be also considered a metal-treated carbon black or a metal-treated carbon black aggregate.

The metal-treated carbon black includes one metal-containing region concentrated at or near the surface of the aggregate (but still constituting part of the aggregate) or within the aggregate. The metal-treated carbon black thus comprises two phases, one of which is carbon and the other of which is a metal-containing species. The metal-containing species phase included in the aggregate is not attached to a carbon black aggregate like a silica coupling agent, or coated on to a pre-formed aggregate but actually is part of the same aggregate as the carbon phase. Further, it is within the bounds of the present invention to use more than one type of metal-containing compound in the feedstocks. If more than one type of metal-containing compound is used in the feedstocks, then an aggregate comprising a carbon phase and two or more different metal-containing species phases would be formed. In addition, if a silicon-containing compound is included in one of the feedstocks, then a silicon-containing species phase would also be formed as part of the same aggregate containing the carbon phase and the metal-containing species phase(s). In addition, a boron-containing compound can also be included in the feedstocks, and if present, would form a boron-containing species phase as part of the same aggregate containing the carbon phase and the metal-containing species phase. Accordingly, the metal-treated carbon black formed from the process of the present invention can have two or more different types of metal-containing species phases and/or additional non-metal species phases. The process used to make the aggregate comprising a carbon phase and a silicon-containing species phase can be substantially used to make the aggregate comprising a carbon phase and a metal-containing species phase. See also, U.S. Pat. Nos. 6,150,453 and 6,017,980, which are incorporated in their entirety by reference herein.

The metal-containing species include compounds containing aluminum, zinc, magnesium, calcium, titanium, vanadium, cobalt, nickel, zirconium, tin, antimony, chromium, neodymium, lead, tellurium, barium, cesium, iron, niobium, tantalum, and molybdenum. Preferably, the metal-containing species phase is an aluminum- or zinc-containing species phase. The metal-containing species include, but are not limited to, oxides of metals.

Useful volatilizable compounds (i.e., the metal-containing compounds) include any compound which is volatilizable at carbon black reactor temperatures. Examples include volatilizable or decomposable compounds containing aluminum, zinc, magnesium, cerium, tantalum, niobium, calcium, titanium, vanadium, cobalt, nickel, zirconium, tin, antimony, chromium, neodymium, lead, tellurium, barium, cesium, iron, and molybdenum. Specific examples include, but are not limited to, butoxides such as Aluminum III n-Butoxide and Aluminum III s-Butoxide, and propoxides, such as Al III iso-propoxide. Examples of suitable zinc-containing compounds include, but are not limited to, zinc napthenate and zinc octoate. Other examples include, but are not limited to, tantalum chlorides, niobium chlorides, magnesium ethoxide, magnesium isopropoxide, calcium propoxide, titanium isopropoxide, cobaltous napthenate, tin diethyl oxide, neodymium oxalate, and the like. The flow rate of the volatilizable compound will determine the weight percent of metal in the treated carbon black. The weight percent of the elemental metal (e.g., elemental aluminum or zinc) in the metal-treated carbon black generally ranges from about 0.1% to 99% or more, by weight of the aggregate, and may be adjusted to any desired level, such as 30% by weight to 50% by weight of the aggregate:

Besides volatilizable compounds, decomposable metal-containing compounds which are not necessarily volatilizable can also be used to yield the metal-treated carbon black.

Once the silicon-treated carbon black or metal-treated carbon black is formed or obtained, then the carbon phase that is present in the silicon-treated carbon black or metal-treated carbon black is removed. Preferably, the entire carbon phase is removed such that 0% or about 0% of the carbon phase remains. In one embodiment, the carbon phase may be present in an amount of from about 1 ppm to about 0.1% based on the weight of the particle or aggregate. Furthermore, in other embodiments, residual amounts of the carbon phase may be present due to incomplete removal of the carbon phase. This equally applies to any type of removable template material and further applies to any of the starting material used in the present invention, such as a silica-coated template and the like.

The manner in which the carbon phase is removed from the silicon-treated carbon black or metal-treated carbon black can be a variety of ways. Essentially, any means to remove or gasify the carbon phase can be used such as the application of heat at the appropriate gas composition, such as burning off the carbon phase. The carbon can be removed by gasification for example with $O_2$, air, $CO_2$ and $H_2$ at the appropriate temperatures. Using air or air enriched with oxygen is a preferred method because it reduces the gasification temperature. The gasification method can be similar to the methods used for regeneration of coke or carbon poisoned catalysts as described in Reference 2 and incorporated in its entirety herein. Typically, the burning off of the carbon phase can be done in a conventional furnace or other heating apparatus and the silicon-treated carbon black or metal-treated carbon black can be subjected to sufficient temperatures for sufficient times to burn off the carbon phase of the silicon-treated carbon black or metal-treated carbon black. One example of a furnace or kiln is described in U.S. Pat. Nos. 6,271,501 or 6,105,272, incorporated in its entirety herein. Other examples are a moving grate combustor, vortex combustor fluid-bed combustor and rotary kiln described in Reference 1 and incorporated in its entirety herein. The temperature of the furnace in which the silicon-treated carbon black or metal-treated carbon black is subjected to in order to remove the carbon phase in air is preferably a temperature of from about 300° C. to about 1000° C. and more preferably from about 500° C. to about 900° C. Generally, the silicon-treated carbon black or metal-treated carbon black is subjected to these temperatures for a time needed to substantially or entirely remove the carbon phase from the silicon-treated carbon black or metal-treated carbon black. Again, the above process to remove the removable template material applies to any of the removable template material described in the present invention and is not limited to the particular carbon phase. Equally so, the particular starting material can be any starting material as described herein, and the above process that preferably involves silica-treated carbon black or metal-treated carbon black applies to other starting materials with a removable template.

At this point, once the removable template, such as carbon phase, is removed, the product is preferably silica if a silicon-treated carbon black was initially used or a metal or oxide thereof if the starting product was a metal-treated carbon black. The silica or metal (or oxide) containing product can be processed in any conventional manner in which silica or metal or metal oxide products are processed.

Prior to the removal of the carbon phase, the starting material, such as the silicon-treated carbon black or metal-treated carbon black, can be in any form such as pelletized or unpelletized. For example, the starting material can be dried pelletized, wet pelletized, or in fluffy form prior to being subjected to the removal of the template, such as the carbon phase. Each of these different forms can lead to different morphologies and shapes of the final silica or metal or oxide thereof. When the starting material is pelletized, this will advantageously lead, in preferred embodiments, to metal or metal oxide products which are agglomerated or have granule sizes. For instance, agglomerates ranging in size from about 0.2 mm to about 5 mm can be obtained. Furthermore, the metal or metal oxide products of the present invention, when agglomerated, can be friable and have a very low crush strength. With conventional silica, it is very difficult to obtain agglomerated or pelletized silica without affecting the properties of the silica. For instance, when fume silica is agglomerated after formation, the dispersing of the pellets can be quite difficult due to the high pellet strength or crush strength. Unlike conventional silica or other metal oxides, the metal or metal oxides of the present invention, when agglomerated, can have a low crush strength or low pellet strength such that the metal or metal oxide agglomerated products are easily crushable and/or dispersible. Examples of crush strengths which can be achieved with the agglomerated metal or metal oxide products of the present invention include, but are not limited to, from about 200 grams or less, such as from about 50 grams or less with respect to average crush strength, and more preferably, from about 5 grams to 100 grams, such as from about 10 grams to 50 grams, as measured by the test set forth in U.S. Pat. No. 4,308,073. The average crush strength for the granules made by the present invention can have an average crush strength distribution wherein at least 50 percent of the agglomerated metal or metal oxides have an average crush strength below 100 grams and more preferably at least 80 percent of the agglomerated metal or metal oxides have an average crush strength of below 100 grams. More preferably, the same distribution percentages would apply to an average crush strength of 75 grams or less, such as from 25 grams to less than 75 grams of average crush strength.

In one of the preferred processes of the present invention, the primary location of the carbon phase and the primary location of the silicon-containing species phase or metal-containing species phase can be anywhere in the overall silicon-treated carbon black or metal-treated carbon black. Preferably, the carbon phase is used as the nuclei or core so that the silicon-containing species phase or metal-containing species phase is formed at least partially, or entirely around the carbon phase; in essence, forming a type of core-shell co-fumed structure. By doing so, the silica or metal or metal oxide particles that are ultimately recovered achieves the most practical surface area and other morphology benefits. In addition, by doing so, there will be less risk of the carbon phase being trapped amongst silica or metal or metal oxides during the removal of the carbon phase. In one embodiment, the carbon phase is formed to act as a template and the silicon-containing or metal-containing species phase is formed at least partially or entirely on this carbon phase template (which may contain silicon- or metal-containing species). By doing so, the shape and morphology and other characteristics can be controlled, and the shape and other characteristics of the carbon phase can be obtained.

In the preferred process, a multi-stage reactor is used wherein the introduction of the first feedstock is primarily, if not exclusively, a carbon black yielding feedstock. Furthermore, the second feedstock in a two-stage process or a multi-stage process is preferably a silicon-containing compound or a metal-containing compound primarily or exclusively. In addition, in a multi-stage process, the third or any subsequent stages would preferably be also a silicon-containing compound or metal-containing compound that provides additional silicon-containing or metal-containing species phases.

In one embodiment of the present application, a very inexpensive carbon black yielding feedstock (or other removable template material) can be used, such as low grade fuel or hydrocarbons which permits a very inexpensive final product to be formed. Using an inexpensive feedstock can lead to further impurities being present in the final product of silica, metal, or metal oxide. However, if these impurities do not affect the overall user application of the silica, metal, or metal oxide thereof, there would be no disadvantage to using an inexpensive carbon black-yielding feedstock. On the other hand, if low impurities are desired in the final product of silica, metal, or metal oxide thereof, then a high grade carbon black-yielding feedstock with low impurities can be used, such as a feedstock having low ash, sulfur, nitrogen, and/or metal content. This will lead to a very high purity silica, metal, or metal oxide. High purity silica, metal, or metal oxide thereof can be achieved on the order of 99% purity, 99.5% purity, 99.9% purity, or higher, such as 99.99% purity or higher with respect to the final product, namely silica, metal, or the metal oxide thereof.

In the process, the final product of silica, metal, or metal oxide thereof by the removal of the removable template can be achieved in a continuous process. In other words, the entire process can involve a reactor which first forms the starting material, such as the silicon-treated carbon black or metal-treated carbon black, and then in a continuous process, the starting material, such as the silicon-treated carbon black or metal-treated carbon black, can be subjected to a removal step which removes the template, such as the carbon phase, such as by heating. On the other hand, the starting material, such as the silicon-treated carbon black or metal-treated carbon black, can be created and then at the appropriate time which can be at any time thereafter, be subjected to the removal of the removable template, such as the carbon phase, such as by heating. Thus, the process of the present invention can be a continuous process, semi-continuous process, a batch process, or a discontinuous process.

The metal or oxides thereof (e.g., silica) of the present invention can be subjected to chemical modification using the means common in the art, such as reactions with chlorosilanes, alkoxysilanes, alkylalkoxysilanes, silazanes, silicone oils, polysiloxanes and cyclic polysiloxanes. The metal or oxides thereof (e.g., silica) can be chemically modified in the same manner as conventionally known with respect to conventional silica, conventional metal, and/or conventional metal oxides. For instance, the chemical modifications described in U.S. Pat. Nos. 6,384,125; 6,342,560; 5,116,886; 5,908,660; and 6,051,672 can be used with the material of the present invention and these patents are incorporated in their entirety by reference herein.

The metal or oxides thereof (e.g., silica) of the present invention can be used in any conventional application, such as in elastomers, reinforcing agents, and the like. For instance, the silica can be an aerogel, hydrophobic, hydrophilic, and the like. It can also be used in applications utilizing its shell or platelet type morphology, such as a carrier of liquids or for controlled release. Further, in a polymer matrix, it can be a barrier to the diffusion of gas or liquid through the filled matrix. As further examples, the metal or oxides thereof (e.g., silica) can be used in pharmaceutical products, such as drugs, and can assist in or provide time-released properties of the active ingredient. In addition, the materials of the present invention can be used in household products, such as perfumes, cosmetics, like make-up (e.g., lipstick, lip balm, mascara, rouge, and the like), deodorants, cleaning products, and the like. The materials of the present invention can be used in a variety of formulations or compositions for numerous uses. The materials of the present invention can be used as fillers and/or carriers of various ingredients, such as colorants (e.g., dyes, and/or pigments), botanical extracts, medicaments, fragrance, such as fragrances oils, antimicrobial ingredients, antiperspirant ingredients, flavors or flavorings, conditioning agents, sunscreen agents, sun tanning ingredients, oils, and the like. Specific examples of uses are set forth in the Examples below. The materials of the present invention can be used as an ingredient in conditioning agents for skin or hair, skin lotions, such as sun tan or sun screens, hand creams or hand lotions, toothpaste, mouthwash, foods including gum, antiperspirant products, antimicrobial products, fragrances such as perfumes and colognes, shampoos, coloring agents, medicines, and the like. As shown in some of the examples of the present invention, various active ingredients can be loaded into or onto the materials of the present invention by any technique such as loading with the use of a carrier or solvent such as water, alcohol, and the like. Organic solvents or inorganic solvents which are preferably volatile can be used as a mechanism to dissolve/disperse/carry the active ingredient(s) and thereby load the materials of the present invention with the active ingredient(s). The volatile solvent can optionally then be removed by standard removal techniques including the application of heat and the like. Any loading level can be used depending on the desirability of the amount of active ingredient in the formulation or composition. The material of the present invention can be used in amounts conventional with respect to this ingredient for the particular use. The metal and metal oxides of the present invention can be used, for instance, as the metal or metal oxide in the compositions/uses described in U.S. Pat. Nos. 6,893,649; 6,887,494; 6,825,259; 6,821,942; 6,818,087; 6,812,192; 6,793,913; 6,780,422; 6,743,756; 6,740,315; 6,737,048; 6,726,916; 6,726,900; 6,716,418; 6,696,049; 6,676,719; 6,673,863; 6,660,289; 6,649,154; 6,645,475; 6,548,170; 6,541,017; 6,534,044; 6,524,598; 6,517,823; 6,517,820; 6,514,505; 6,511,672; 6,939,921; 6,932,132; 6,903,155; 6,902,715; 6,872,772; 6,582,866; 6,287,242; 6,214,507; 6,210,851; 6,230,960; 6,124,071; 6,071,665; 6,001,524; 5,804,349; 5,510,220; 5,378,574; 3,939,087; 4,640,882; and 6,822,043, all incorporated in their entirety by reference herein.

The metal or oxide thereof can be used in the formation of capacitor components such as a capacitor anode. For instance, the metal or oxide thereof can be used in capacitor anodes as describe in U.S. Pat. Nos. 6,348,113; 6,689,187; 6,788,525; 5,986,877; 5,448,447; 4,645,533; 6,420,043; 6,702,869; 6,639,787; 6,592,740; 6,576,099; and 6,322,912, incorporated in their entirety herein by reference. Other uses for the metal or oxides thereof (e.g., silica) include, but are not limited to, elastomers (e.g., elastomers with improved clarity), polymers (with at least one polymer), inks (with at least one colorant), coatings, toners, molecular sieves, anti-caking agents (with at least one ingredient), thermal insulation, fluid thickeners, and the like.

The metal or oxides thereof (e.g., silica) of the present invention can be used in the same manner, using the same incorporation techniques, the same amounts, as used conventionally for these applications.

The material of the present invention, e.g., spherical silica shells, has created the opportunity to formulate and reformulate many personal care products using this new material as a vehicle for some of the functional and physiologically active materials that are used in these products. Similarly, pharmaceutically active materials can be incorporated in the shells and subsequently used in products in order to control the release or improve the stability of material in the finished product. In addition, the shells can be used to sequester ingredients and thereby control their release. The shells can be colored to produce appealing visual effects and/or to act as indicators of site application.

EXAMPLES

Example A

A metal oxide of the present invention was made by using a starting material, which is an aggregate having a carbon phase and a silicon-containing species phase (i.e., Carbon Silica Dual Phase (CSDP) materials), which was prepared in the multistage process described in U.S. Pat. No. 6,709,506 B2.

Table A below lists examples of the starting materials and their analytical properties:

TABLE A

| Sample | $I_2$No (mg/g) | CDBP, ml/100 g | Si wt % | BET area, $m^2/g$ | t-Area, $m^2/g$ | S-factor |
|---|---|---|---|---|---|---|
| CSDP-a | 96 | 103.3 | 8.40 | 185.6 | 149.4 | 0.48 |
| CSDP-b | 48 | 110 | 9.40 | 121.3 | 104.4 | 0.60 |
| CSDP-c | 61.5 | 108.00 | 10.20 | 150 | 119.7 | 0.59 |
| CSDP-d | 49.4 | 104.5 | 14.80 | 157.7 | 119.6 | 0.69 |

The S-factor in the Table A is defined as one minus the ratio of the Iodine adsorption number (mg/g) and BET area ($m^2/g$) of the starting material as:

$$S = 1 - I_2\text{No}/\text{BET}$$

The iodine in the Iodine adsorption number test does not adsorb on the silica surface. A comparative example is that the $I_2$No on fumed silica (HS-5), that has a BET surface area of 340 $m^2/g$, has a negligible $I_2$No of 0.5. The S-factor can be used in this invention as one way to make a certain type of product and/or define the completeness of the shell that results after the template is removed. When the S factor is small, the silica containing phase would track the portions of the shape of the template and produce incomplete shells, and when the S factor is high and close to 1, the silica containing phase will track substantially the shape of the template and produce a more complete shell. A compressed DBP oil adsorption measurement (CDBP) of the starting material can be used to estimate the structure of the template.

The template can be characterized as well by BET and t-area after HF extraction. Table B has the BET and t-area data after silica extraction with HF:

TABLE B

| Sample | BET HF area, $m^2/g$ | t-Area HF, $m^2/g$ |
|---|---|---|
| CSDP-a | 200 | 179.8 |
| CSDP-b | 124 | 116 |
| CSDP-c | 173 | 155 |
| CSDP-d | 194.3 | 175 |

The ash silica shells (CS) of the following example were prepared similar to the procedure described in ASTM D1506- method A by removing carbon containing material by exposing it to air at 600° C. The data is reported in Table C.

TABLE C

| Sample | Ash-BET area, m²/g |
|---|---|
| CSDP-a (CS-a) | 669.9 |
| CSDP-b (CS-b) | 435 |
| CSDP-c (CS-c) | 645 |
| CSDP-d (CS-d) | 532 |

The BET ($N_2$) surface area was measured following the procedure described in ASTM D4820-method B.

Iodine number was measured following the procedure described in ASTM D1510-05.

The external surface area (t-area) was measured following the samples preparation and measurement procedure described in ASTM D3037—Method A for Nitrogen surface area. For this measurement, the nitrogen adsorption isotherm was extended up to 0.55 relative pressure. The relative pressure is the pressure (P) divided by the saturation pressure (P0) (the pressure at which the nitrogen condenses). The adsorption layer thickness (t1) was then calculated using the relation:

$$t_1 = \frac{13.99}{\sqrt{(0.034 - \log(P/P_0))}}$$

The volume (V) of nitrogen adsorbed was then plotted against t1. A straight line was then fitted through the data points for t1 values between 3.9 and 6.2 Angstroms. The t-area was then obtained from the slope of this line as follows:

$t$-area, m²/gm=15.47×slope

The HF (hydrofluoric acid) treatment of the samples were carried out using 5% v/v concentration of HF at boiling temperature for 1 h. After the treatment, the samples were washed on a filter 20 times with water and thereafter the washed carbon blacks were dried in preparation for further analysis.

Example B

Ashed silica shells were also prepared in a lab 4" fluidized bed reactor. About 1 lb. of dry granulated starting material, CSDPF-c, was loaded into the fluid bed reactor and 1.45 m³/hr of air flow was established at the bed where the temperature was 830° C. Bed temperature was monitored in several locations. Fluidization air was decreased slightly when at the end of the carbon phase removal, the upper bed temperature began to drop. The ashed silica shell material produced in the fluid bed process, CE0503, had a BET of 530 m²/g and had the appearance of white granules retaining the shape of the original dry pellets. The material in Table D was compared with fumed silica, HS-5. The silica shell material had almost a 200% higher manual DBP adsorption number (594 ml/100 g) compared to fumed silica HS-5. The manual DBP oil absorption test was done according to ASTM-D281-95.

TABLE D

| Sample | BET area, m²/g | Tamped Density, g/L | Manual DBP, ml/100 g |
|---|---|---|---|
| CE0503 | 506 | 119.6 | 594 |
| HS-5 | 325 | 50 | 298 |

This material CE0503 was used below in the following examples.

Examples 1-3

Some comparisons were made to the similarly sized Nanogel 01N, although this product is hydrophobic as opposed to the hydrophilic silica shells. Evaluations studied the use of the shells of the present invention as a fragrance reservoir to extend the longevity for environmental applications.

| | Examples | | |
|---|---|---|---|
| Ingredients | 1 gms | 2 gms | 3 gms |
| Nanogel 01N | 0.50 | — | — |
| Silica Shells (CE0503) | — | 0.50 | — |
| Bounty ® Paper Towel | — | — | 0.50 |
| Fragrance Oil (Wildflower #94720 - AFF) | 2.00 | 2.00 | 2.00 |

Examples 1 and 2 retained 44% and 43.5% fragrance oil, respectively, while the paper in Example 3 retained 38% fragrance oil after two weeks air exposure. This shows that the silica shells act as reservoirs (for the fragrance oil) and are equal to or more effective than paper.

Examples 4-7

These experiments studied techniques for "loading" the shells.

| | Examples | | | |
|---|---|---|---|---|
| Ingredients | 4 gms | 5 gms | 6 gms | 7 gms |
| Nanogel 01N | 0.40 | — | 0.40 | — |
| Silica Shells (CE0503) | — | 0.40 | — | 0.40 |
| Ethanol 3A (200 proof) | 5.00 | 5.00 | — | — |
| Deionized Water | — | — | 5.00 | 5.00 |

In Examples 4, 5, and 7 the spheres were just wetted by the liquid leaving little, if any, free liquid. In Example 5 the Nanogel was not wetted by the water. The samples were air dried for 2 days. Examples 4 and 5 appeared unchanged and were comparable to virgin material. Example 6 showed an area of powdered material where the water had pooled and, evidently disrupted the Nanogel structure. Example 7 had a smaller (by eyeball) sphere diameter and the shells were noticeably harder and less friable when compared to virgin shells and to the dried Example 5. Ethanol or isopropanol (IPA) were used in further sphere loading studies.

This method is not intended to limit the methods available to load the shells. Certainly, one can use other solvents: such as volatile alkanes, alkenes and alkynes, other lower alcohols such as propanol and butanol, lower ketones such as acetone and methyl ethyl ketone, ethers such as Glyme, Diglyme and diethyleneglycol ethyl ether, aromatic solvents such as benzene, xylene and toluene, volatile silicones such as tetra, penta and hexa cyclomethicones and the lower (from about 2 to about 10) linear dimethylsiloxanes, fluoro and hydro fluoro compounds as well as specific techniques such as powder blending machinery having liquid addition methods, fluid bed mixing with liquid addition methods, liquid-powder blending mixers (both active and static) combined with any one of various drying methods such as open air, ovens, mobile belt dryers, spray driers and fluid bed driers.

The preferred method in the examples for loading the shells was to weigh the shells, separately dissolve all of the ingredients in IPA (or ethanol or water or combinations) and pour this mixture onto the shells. The shells were allowed to stand for 2 to 3 minutes with the mixture and were then poured into a conical paper filter (Ahlstrom 615). The container was rinsed into the filter with ~10 ml solvent (water or IPA as specified) and allowed to drain for about ten minutes. The filter paper was then opened carefully to preserve the shells and placed upon a quarter folded paper towel to air dry for at least 6 hours.

Examples 8-11

The following examples illustrate the loading technique and help to define the expected results.

| Ingredients | Examples | | | |
|---|---|---|---|---|
| | 8 gms | 9 gms | 10 gms | 11 gms |
| Silica Shells (CE0503) | 0.25 | 0.25 | 0.25 | 0.25 |
| FD&C Blue No. 1 (1% aq soln.) | 0.10 | 0.10 | — | — |
| Benzalkonium Chloride | — | — | 1.00 | — |
| Aluminum Chlorohydrate (50% aq) | — | — | — | 1.00 |
| Isopropanol | — | 3.00 | — | — |
| Deionized Water | 3.00 | — | 2.00 | 4.00 |

Examples 8 and 9 show the differences resulting from the use of water or IPA as a solvent. In particular, the dye solution was added to the shells before the addition of the solvent resulting in non-uniform color distribution. This effect is easily overcome (if desired) by adding the dyes to the solvent before addition to the shells. More importantly, the Example 8 shells contained appreciable amounts of powder and were generally smaller in size than untreated shells, while the Example 9 shells had little powder and the shells were comparable in size to virgin shells. Treatment with water to load the shells causes them to become smaller and to disintegrate upon drying.

Examples 10 and 11 show the loading of the shells with a cationic antimicrobial and an antiperspirant ingredient. Both Examples showed retention of the cationic product. A small quantity of the loaded shells was rubbed onto an area of the volar forearm; the area was rinsed lightly with running tap water and then sprayed with a 0.1% aq. solution of FD&C Blue No. 1. When the blue dye solution was rinsed off, it was apparent that the areas where the examples had been rubbed were darker than the surrounding skin. This shows that the cationic benzalkonium chloride and aluminum chlorohydrate were loaded in the shells, were released by rubbing and retained there cationic functionality in sufficient degree to react with the anionic dye, FD&C Blue No. 1.

Examples 12-15

| Ingredients | Examples | | | |
|---|---|---|---|---|
| | 12 gms | 13 gms | 14 gms | 15 gms |
| Silica Shells (CE0503) | 0.25 | 0.25 | 0.25 | 0.25 |
| Tutti Fruity Flavor (ACR1562020B) | 0.50 | — | — | — |
| FD&C Blue No. 1 (1% aq soln.) | — | 0.05 | 0.05 | — |
| Dicetyldimonium Chloride | — | 1.00 | — | — |
| Sodium Lauryl Sulfate (30%) | — | — | 1.00 | — |
| Citric Acid | — | — | — | 1.00 |
| Ethanol 3A 200 proof | 2.50 | — | — | — |
| Isopropanol | — | 2.00 | 2.00 | 1.50 |
| Deionized Water | — | — | — | 1.00 |

Example 12 retains acceptable flavor and shell integrity. In Example 13, the shells are smaller upon drying, but still friable and they release the cationic onto skin leaving a soft powdery feel after rinsing and drying.

The shells in Example 14 are the same size as the virgin shells. They are friable and readily release the surfactant to provide foaming, wetting and some abrasiveness when wetted and rubbed on the hands.

There is appreciable powder in the Example 15 spheres, although the majority of the shells are intact and the same size as the virgin shells. A 7 wt % aqueous dispersion of Example 15 had a pH of 2.16, while an 8 wt % dispersion of the virgin shells had a pH of 5.08.

Examples 16-19

| Ingredients | Examples | | | |
|---|---|---|---|---|
| | 16 gms | 17 gms | 18 gms | 19 gms |
| Silica Shells (CE0503) | 0.25 | 0.25 | 1.00 | 1.00 |
| Chocomint (ACR1562031) AFF | 0.50 | — | — | — |
| D&C Brown #1 Replacement (1% aq. solution) | 0.05 | — | — | — |
| Sodium Saccharin | 0.20 | — | — | — |
| Sodium Bicarbonate | — | 0.50 | — | — |
| Ascorbic Acid | — | — | 1.00 | — |
| Apricot Kernel Oil | — | — | — | 9.00 |
| Ethanol 3A 200 proof | 2.00 | — | — | — |
| Isopropanol | — | — | 6.00 | — |
| Deionized Water | 1.00 | 2.00 | 4.00 | — |

Example 16 had a noticeable chocolate/mint flavor and sweetness. The shells are about the same size as virgin shells and there is very little powder. 0.20 grams of the dried Example 16 was added to Colgate Total brand toothpaste by slow stirring with a glass rod. After sitting for six hours (to hydrate the shells) the color had bled considerably, but the toothpaste color was still variegated. The shells were apparent upon brushing as soft masses that yielded extra sweetness and a chocolate flavor when they were smashed during brushing. After several days standing, the shell masses were still noticeable, and the color and sweetness had uniformly dispersed.

The dried shells of Example 17 were smaller than the virgin shells and there was a noticeable amount of fines. 0.25 grams of Example 17 was combined with 0.19 grams of Example 15 as dried shells. Ten grams of water was added resulting in a slow evolution of gas bubbles with some of the shells rising to the water surface, losing gas and sinking. Other shells floated, while still others remained on the bottom. This demonstrates that both the sodium bicarbonate and the citric acid were successfully loaded in the shells and both were released by the water and remained capable of reaction.

The dried shells of Example 18 were opaque white spheres, about the same size as the virgin shells and with very little powder. The final dried weight of Example 18 was 3.36 grams. The taste of the loaded shells was acidic and the pH of a 10% dispersion was 2.80 showing that ascorbic acid can be loaded in the shells and subsequently released by water.

Example 19 was a free flowing mixture of white and light tan colored spheres that were similar to the virgin shells in size. The final dried weight of Example 19 was 4.60 grams. They were dry to the touch, but yielded oil when smashed on the skin. Smashing the Example 19 shells produced an oily mass that was readily washed from the skin and left an oily film—much like a hand cream or lotion.

In addition to the toothpaste example, some of the examples of loaded shells were used to make personal care products or were added to existing personal care products to modify their properties.

Examples 20-21

| | Examples | |
|---|---|---|
| Ingredients | 20 gms | 21 gms |
| Silica Shells (CE0503) | 1.00 | 1.00 |
| Dicetyldimonium Chloride | 4.00 | — |
| Sodium Lauryl Sulfate (30%) | 4.00 | 4.00 |
| FD&C Blue No. 1 (1% aq soln) | 1 drop | 1 drop |
| D&C Red No. 33 (1% aq soln) | 1 drop | — |
| FD&C Yellow No. 5 (1% aq soln) | — | 1 drop |
| Isopropyl Alcohol (#1) | 6.00 | 6.00 |
| Isopropyl Alcohol (#2) | 6.00 | — |

Example 20 was made by weighing the shells, combining the Dicetyldimonium Chloride, IPA (#1) and Blue 1 and adding this mixture to the shells, allowing the mixture to stand for 2-3 minutes, filtering the shells using IPA to rinse the container. Next the Sodium Lauryl Sulfate (30%), Red 33 and IPA (#2) were combined and poured over the filtered, but still damp, shells using IPA to rinse the container. When the filtrate stopped dripping, the filter was removed from the funnel and placed upon a quarter folded paper towel to air dry. The dried weight of Example 20 was 3.15 grams, the color was light violet and the spheres were about the same size as the virgin shells, although there was a lot of clumping of the spheres. These clumps were quite soft and readily broke apart upon manipulation. The intention of this Example was to create loaded shells that contain cationic conditioning agents that are then sequestered in the shells by reaction with an oppositely charged entity in order to prevent (or at least control) the release into an anionic shampoo.

Example 21 was made in the same manner as described for Example 20, except that only one solution, the anionic surfactant Sodium Lauryl Sulfate, was added to the shells. The dried weight of Example 21 was 3.18 grams, the color was light green and the spheres were about the same size as the virgin shells and they were opaque. These shells wet easily and produce foam readily when rubbed between wetted hands and they have a pleasant abrasive feel.

One gram of Example 20 was added to 19 grams (5% w/w) of NO-AD Tangerine & Ginseng Aroma Hair Care Therapy Shampoo. The shampoo is a transparent clear, orange colored cleaning formula. The addition of Example 20 initially changed the color of the base shampoo to a muddy violet. After three days, the shampoo was opaque and violet in color. The shells were evident as white to translucent spheres—readily visible and intact in the shampoo. On washing, the shells could be readily felt and, although they were softer than they were when initially added, they were still somewhat gritty feeling. The foaming of the shampoo had been increased by the addition of Example 20 but there was no noticeable increase in conditioning.

One gram of Example 21 was added to 19 grams (5% w/w) of NO-AD Tangerine & Ginseng Aroma Hair Care Therapy Shampoo. The shampoo is a transparent clear, orange colored cleaning formula. The addition of Example 21 initially changed the color of the base shampoo only slightly. After three days, the shampoo remained clear and was olive green in color. The shells were evident as white to translucent spheres—readily visible and intact in the shampoo. On washing, the shells could be readily felt and, although softer than they were when originally added, they were still somewhat gritty feeling. The foaming of the shampoo had been increased by the addition of Example 21 and there was a noticeable increase in the detergent like feel of the shampoo.

NO-AD Shampoo Ingredient Listing: Water, Sodium Laureth Sulfate, Cocamide DEA, Cocamidopropyl Betaine, TEA-Lauryl Sulfate, Cinnamidopropyl Trimonium Chloride, Sorbitol, Glycerin, Panax Ginseng Root Extract, Citrus Nobilis (Mandarin Orange) Peel Extract, Fragrance, Propylene Glycol, DMDM Hydantoin, Methylparaben, Propylparaben, Disodium EDTA, Red 4, Yellow 6.

In another application, Example 11 was remade using IPA as the solvent instead of water.

Examples 22-23

| | Example | |
|---|---|---|
| Ingredients | 22 gms | 23 gms |
| Silica Shells (CE0503) | 1.00 | 1.00 |
| Aluminum Chlorohydrate (50% soln) | 4.00 | 4.00 |
| Isopropanol | 4.00 | 4.00 |
| FD&C Blue No. 1 (1% aq soln) | — | 1 drop |

The dried weight was 2.58 grams and the shells were opaque white and somewhat smaller than the virgin shells.

Example 22 was dispersed in a base composed of Dermolastic™ Silicone Gel polymer dispersed in isododecane (IDD). In a second experiment, Examples 24-25

| Ingredients | Examples | |
| --- | --- | --- |
| | 24 gms | 25 gms |
| Example 22 air dried | 2.50 | — |
| Example 23 air dried | — | 1.50 |
| Dermolastic ™ Silicone Polymer in IDD | 3.00 | — |
| Isododecane | 9.00 | — |
| Dermolastic ™ Silicone Polymer in D5 | — | 2.00 |
| Pentasiloxane | — | 6.30 |
| Fragrance (AFF 147178) | 0.50 | 0.20 |

These are intended as antiperspirant products. Physically, they are soft gels with suspended solid shells that are visible as translucent to clear particles. This formulation could be improved by softening the shells with glycols, water or combinations of glycols and water. In addition, adding impalpable aluminum chlorohydrate powder (or other similar impalpable antiperspirant powders) to the Dermolastic™ solvent gel would improve efficacy and, if the particles are small enough, they would not noticeably reduce the clarity of the Dermolastic™ gel matrix. Additionally, other acceptable antiperspirant materials could also be added to the shells instead of aluminum chlorohydrate. The shells could also be colored with acceptable colorants in order to enhance the appearance of the finished formula as in Example 23.

Examples 26-28

| Ingredients | Example | | |
| --- | --- | --- | --- |
| | 26 gms | 27 gms | 28 gms |
| Silica Shells (CE0503) | 1.00 | 1.00 | 1.00 |
| Apricot Kernel Oil | 9.00 | — | — |
| Dimethicone (1,000 cps) | — | 9.00 | — |
| Ethylhexyl Methoxycinnamate | — | — | 9.00 |

The oils were added to the shells, allowed to stand for ½ hour and rinsed from the container into the filter with about 15 mls of IPA. The filter was drained for 15 minutes, and then removed and placed upon a quarter folded paper towel to air dry. The final dried weight of Example 25 was 4.60 grams, the dried weight of Example 26 was 6.81 grams and the dried Example 27 weighed 5.10 grams. These Examples were put into skin lotions with the following formulas.

Examples 29-31

| Ingredients | Example | | |
| --- | --- | --- | --- |
| | 29 % | 30 % | 31 % |
| Behenic Acid | 1.00 | 1.00 | 1.00 |
| Cetearyl Alcohol | 3.00 | 3.00 | 3.00 |
| Meadowfoam Seed Oil | 10.00 | 10.00 | 10.00 |
| Dimethicone (1,000 cps) | 0.50 | 0.50 | 0.50 |
| Deionized Water | 78.70 | 78.70 | 78.70 |
| Xanthan Gum | 0.30 | 0.30 | 0.30 |
| Triethanolamine | 0.30 | 0.30 | 0.30 |
| Phenobact ™ | 1.00 | 1.00 | 1.00 |
| Fragrance (AFF #116778) | 0.20 | 0.20 | 0.20 |
| Example 26 | 5.00 | — | — |
| Example 27 | — | 5.00 | — |
| Example 28 | — | — | 5.00 |

The basic lotion used for Examples 29, 30 and 31 is an anionic formula using Behenic acid. This makes a lotion that has a definite rub-in "break" when the lotion is applied. Examples 29, 30, and 31 all show a delayed and minimized "break" which shows that the "oils" carried by the shells are released by rubbing. The shells can be felt as the lotion is rubbed on the skin, but they readily break and dissipate becoming impalpable. This provides an intriguing tactile effect that can be used as a signal that active ingredients (such as botanical extracts or medicaments) are being applied or that additional emollients are being released. Of course, the shells can be differentially colored (and/or fragranced) to enhance visual and olfactory effects.

One gram of each of Examples 26, 27 and 28 were added to 19 grams (5% w/w) of NO-AD Tangerine & Ginseng Aroma Hair Care Therapy Shampoo. The shampoo is a transparent clear, orange colored cleaning formula. The addition of Example 26 makes the shampoo opaque (Example 32). The shampoo still foams adequately. Triglycerides typically cause a decrease in the foam volume of a shampoo, similar to the defoaming effect of dimethicones, but not as dramatic, and the volume of foam produced by this formula is unanticipated. This product (Example 33) is clear (which is an unanticipated effect), but this product did not foam at all and left a distinct oily emollient feel upon rinsing. The addition of Example 28 to NO-AD shampoo makes the shampoo opaque (Example 34). The shampoo still foams adequately. Fatty emollient esters typically cause a decrease in the foam volume of a shampoo, similar to the defoaming effect of dimethicones, but not as dramatic, and the volume of foam produced by this formula is unanticipated.

Example 35

Two (2) grams of Example 2 shells were added to 8 grams of a 50% polyurethane dispersion of Polyderm™ PEPA (an isophorone diisocyanate/polytetrahydrofuran copolymer) and mixed by shaking to distribute the shells in the polyurethane dispersion. This mixture was poured onto a plastic wrap sheet and allowed to air dry. The result is a clear film of flexible polyurethane polymer with embedded shells containing fragrance that is readily smelled. In addition, mixture poured onto a piece of filter paper also had a noticeable fragrance, was flexible and had numerous shell particles adhering to the surface. This experiment could be the basis for producing novel environmental fragrancing products that could conceivably contain one fragrance in the polyurethane film former and another in the shells. As time passes, the shells would release their fragrance causing an evolution in the character of the fragrance, but maintaining the intensity and environmental impact. Because of the liquid nature of the polymer and shell dispersion, it could be coated or sprayed on to a surface or items could be dipped into the mixture.

Reference 1. Catalyst Deactivation and Regeneration by Calvin Bartholomew,
Brigham Young University
Kirk-Othmer Encyclopedia of Chemical Technology
Copyright © 2003 by John Wiley & Sons, Inc. All rights reserved
Reference 2. Incinerators by R. Bertrum Diemer Jr., E.I. du Pont de Nemours & Co., Inc.
Thomas D. Ellis, E.I. du Pont de Nemours & Co., Inc.
Geoffrey D. Silcox, University of Utah
JoAnn S. Lighty, University of Utah
David W. Pershing, University of Utah
Kirk-Othmer Encyclopedia of Chemical Technology
Copyright © 1995 by John Wiley & Sons, Inc. All rights reserved Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A carrier for liquids comprising at least one liquid contained within a pyrogenic metal or oxide thereof, the pyrogenic metal or oxide thereof having a shell shape or a platelet shape that is non-linear and curved, wherein the pyrogenic metal or oxide thereof has a S-factor of from 0.05 to 0.98.

2. The carrier of claim 1, wherein said pyrogenic metal or oxide thereof is silica.

3. The carrier of claim 1, wherein said pyrogenic metal or oxide thereof has the following properties:
   a) an aspect ratio of from 2 to 150;
   b) a CDBP of from 400 ml/100 g to 1000 ml/100 g; and
   c) a BET surface area of from 300 $m^2/g$ to 1000 $m^2/g$.

4. The carrier of claim 3, wherein said pyrogenic metal or oxide thereof is silica.

5. The carrier of claim 3, wherein said pyrogenic metal or oxide thereof includes broken, irregular, or partial shells.

6. The carrier of claim 1, wherein said pyrogenic metal or oxide thereof is agglomerated.

7. The carrier of claim 1, wherein said pyrogenic metal or oxide thereof is agglomerated and has an average crush strength of 150 grams or less.

8. The carrier of claim 1, wherein said pyrogenic metal or oxide thereof has a BET surface area of 1,050 $m^2/g$ or greater.

9. A carrier for liquids comprising at least one liquid contained within a pyrogenic metal or oxide thereof, the pyrogenic metal or oxide thereof having a shell shape or a platelet shape that is non-linear and curved, wherein said pyrogenic metal or oxide thereof has the following properties:
   a) an aspect ratio of from 2 to 150;
   b) a CDBP of from 400 ml/100 g to 1000 ml/100 g; and
   c) a BET surface area of from 300 $m^2/g$ to 1000 $m^2/g$.

10. A carrier for liquids comprising at least one liquid contained within a pyrogenic metal or oxide thereof, the pyrogenic metal or oxide thereof having a shell shape or a platelet shape that is non-linear and curved, wherein said pyrogenic metal or oxide thereof is agglomerated and has an average crush strength of 150 grams or less.

11. A fluid thickener comprising at least one fluid and a pyrogenic metal or oxide thereof, the pyrogenic metal or oxide thereof having a shell shape or a platelet shape that is non-linear and curved, wherein the pyrogenic metal or oxide thereof has a S-factor of from 0.05 to 0.98 or said pyrogenic metal or oxide thereof has the following properties:
   a) an aspect ratio of from 2 to 150;
   b) a CDBP of from 400 ml/100 g to 1000 ml/100 g; and
   c) a BET surface area of from 300 $m^2/g$ to 1000 $m^2/g$.

12. A cosmetic product comprising a pyrogenic metal or oxide thereof, the pyrogenic metal or oxide thereof having a shell shape or a platelet shape that is non-linear and curved, wherein the pyrogenic metal or oxide thereof has a S-factor of from 0.05 to 0.98 or said pyrogenic metal or oxide thereof has the following properties:
   a) an aspect ratio of from 2 to 150;
   b) a CDBP of from 400 ml/100 g to 1000 ml/100 g; and
   c) a BET surface area of from 300 $m^2/g$ to 1000 $m^2/g$.

13. The cosmetic product of claim 12, wherein said cosmetic product is a perfume or deodorant.

14. A polymer matrix comprising a pyrogenic metal or oxide thereof, the pyrogenic metal or oxide thereof having a shell shape or a platelet shape that is non-linear and curved, wherein the pyrogenic metal or oxide thereof has a S-factor of from 0.05 to 0.98 or said pyrogenic metal or oxide thereof has the following properties:
   a) an aspect ratio of from 2 to 150;
   b) a CDBP of from 400 ml/100 g to 1000 ml/100 g; and
   c) a BET surface area of from 300 $m^2/g$ to 1000 $m^2/g$.

15. A capacitor comprising a pyrogenic metal or oxide thereof, the pyrogenic metal or oxide thereof having a shell shape or a platelet shape that is non-linear and curved, wherein the pyrogenic metal or oxide thereof has a S-factor of from 0.05 to 0.98 or said pyrogenic metal or oxide thereof has the following properties:
   a) an aspect ratio of from 2 to 150;
   b) a CDBP of from 400 ml/100 g to 1000 ml/100 g; and
   c) a BET surface area of from 300 $m^2/g$ to 1000 $m^2/g$.

16. An elastomer composition comprising a pyrogenic metal or oxide thereof and at least one elastomer, the pyrogenic metal or oxide thereof having a shell shape or a platelet shape that is non-linear and curved, wherein the pyrogenic metal or oxide thereof has a S-factor of from 0.05 to 0.98 or said pyrogenic metal or oxide thereof has the following properties:
   a) an aspect ratio of from 2 to 150;
   b) a CDBP of from 400 ml/100 g to 1000 ml/100 g; and
   c) a BET surface area of from 300 $m^2/g$ to 1000 $m^2/g$.

17. An ink or toner comprising at least one colorant and a pyrogenic metal or oxide thereof, the pyrogenic metal or oxide thereof having a shell shape or a platelet shape that is non-linear and curved, wherein the pyrogenic metal or oxide thereof has a S-factor of from 0.05 to 0.98 or said pyrogenic metal or oxide thereof has the following properties:
 a) an aspect ratio of from 2 to 150;
 b) a CDBP of from 400 ml/100 g to 1000 ml/100 g; and
 c) a BET surface area of from 300 $m^2$/g to 1000 $m^2$/g.

18. Thermal insulation comprising a pyrogenic metal or oxide thereof, the pyrogenic metal or oxide thereof having a shell shape or a platelet shape that is non-linear and curved, wherein the pyrogenic metal or oxide thereof has a S-factor of from 0.05 to 0.98 or said pyrogenic metal or oxide thereof has the following properties:
 a) an aspect ratio of from 2 to 150;
 b) a CDBP of from 400 ml/100 g to 1000 ml/100 g; and
 c) a BET surface area of from 300 $m^2$/g to 1000 $m^2$/g.

19. A matrix comprising a pyrogenic metal or oxide thereof, wherein the matrix is a barrier material against liquids and/or gases, the pyrogenic metal or oxide thereof having a shell shape or a platelet shape that is non-linear and curved, wherein the pyrogenic metal or oxide thereof has a S-factor of from 0.05 to 0.98 or said pyrogenic metal or oxide thereof has the following properties:
 a) an aspect ratio of from 2 to 150;
 b) a CDBP of from 400 ml/100 g to 1000 ml/100 g; and
 c) a BET surface area of from 300 $m^2$/g to 1000 $m^2$/g.

* * * * *